US006216021B1

United States Patent
Franceschini et al.

(10) Patent No.: US 6,216,021 B1
(45) Date of Patent: Apr. 10, 2001

(54) METHOD FOR MEASURING ABSOLUTE SATURATION OF TIME-VARYING AND OTHER HEMOGLOBIN COMPARTMENTS

(75) Inventors: Maria Angela Franceschini; Sergio Fantini; Enrico Gratton, all of Urbana, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 0 days.

(21) Appl. No.: 09/326,779

(22) Filed: Jun. 4, 1999

(51) Int. Cl.$^7$ ...................................................... A61B 5/00

(52) U.S. Cl. ............................................................ 600/310

(58) Field of Search .................................... 600/310, 322, 600/323, 328, 330, 336, 473, 476

(56) References Cited

U.S. PATENT DOCUMENTS

| | | | |
|---|---|---|---|
| 4,759,369 | 7/1988 | Taylor .................................. | 128/633 |
| 5,413,100 | 5/1995 | Barthelemy et al. ................ | 128/633 |
| 5,431,159 | 7/1995 | Baker et al. ......................... | 128/633 |
| 5,497,769 | * 3/1996 | Gratton et al. ....................... | 600/323 |
| 5,575,285 | 11/1996 | Takanashi et al. ................... | 128/633 |
| 5,706,821 | * 1/1998 | Matcher et al. ..................... | 600/310 |
| 5,782,755 | * 7/1998 | Chance et al. ....................... | 600/322 |
| 5,800,349 | * 9/1998 | Isaacson et al. ..................... | 600/323 |

OTHER PUBLICATIONS

Y. Mendelson, "Pulse Oximetry: Theory and Applications for Noninvasive Monitoring", *Clinical Chemistry*, vol. 38, No. 9, 1992, pp. 1601–1604.

R.K. Webb, A.C. Ralston, W.B. Runciman, "Potential Errors in Pulse Oximetry", *Anaesthesia*, vol. 46, 1991, pp. 207–212.

M. Kohl, C. Nolte, H.R. Heekeren, S. Horst, U. Scholz, H. Obrig, A. Villringer, "Changes in Cytochrome–Oxidase Oxidation in the Occipital Cortex During Visual Stimulation: Improvement in Sensitivity by the Determination of the Wavelength Dependence of the Differential Pathlength Factor", *Proc. SPIE* 3194, 1998, pp. 18–27.

M. Kohl, C. Nolte, H.R. Heekeren, S. Horst, U. Scholz, H. Obrig, A. Villringer, "Determination of the Wavelength Dependence of the Differential Pathlength Factor from Near–Infrared Pulse Signals", *Phys. Med. Biol.*, vol. 43, 1998, pp. 1771–1782.

D.A. Benaron, W.E. Benitz, R.L. Ariagno, D.K. Stevenson, "Noninvasive Methods for Estimating In Vivo Oxygenation", *Clinical Pediatrics*, May 1992, pp. 258–273.

(List continued on next page.)

Primary Examiner—Eric F. Winakur
Assistant Examiner—Joseph A. Cadugan
(74) Attorney, Agent, or Firm—Greer, Burns & Crain, Ltd.

(57) ABSTRACT

The present invention involves a time-resolved measurement method for the real time, non-invasive, simultaneous measurement of time-varying and other hemoglobin compartment saturation. This capability achieves absolute pulse oximetry and oximetry for tissue, without calibration based on a population of healthy people. Calculations conducted by the invention use quantitative measurement of tissue absorption spectrum for tissue saturation, and an amplitude of absorption oscillations for the time-varying hemoglobin compartments at various wavelengths. The invention illuminates tissue and senses light at predetermined distances apart on the tissue to be measured. Intensity and phase data are acquired from source-detector pairs to calculate absolute tissue optical properties from time-resolved measurement data, namely, a reduced scattering coefficient and an absorption coefficient. To determine time-varying hemoglobin compartment saturation, an amplitude is quantitatively calculated of absorption oscillations correlating variations of an average intensity of the source and detector pair by using the time-resolved measurement data.

15 Claims, 6 Drawing Sheets

OTHER PUBLICATIONS

A.C. Ralston, R.K. Webb, W.B. Runciman, "Potential Errors in Pulse Oximetry", *Anaesthesia*, vol. 46, 1991, pp. 202–206.

D.L. Reich, A. Timcenko, C.A. Bodian, J. Kraidin, J. Hofman, M. DePerio, S.N. Konstadt, T. Kurki, J.B. Eisenkraft, "Predictors of Pulse Oximetry Data Failure", *Anesthesiology*, vol. 84, No. 4, Apr. 1996, pp. 859–864.

C.F. Poets, D.P. Southall, "Noninvasive Monitoring of Oxygenation in Infants and Children: Practical Considerations and Areas of Concern", *Pediatrics*, vol. 93, No. 5, May 1994, pp. 737–746.

A.T. Costarino, D.A. Davis, T.P. Keon, "Falsely Normal Saturation Reading with the Pulse Oximeter", *Anesthesiology*, vol. 67, No. 5, Nov. 1987, pp. 830–831.

D.M. Orenstein, S.E. Curtis, P.A. Nixon, E.R. Hartigan, "Accuracy of Three Pulse Oximeters During Exercise and Hypoxemia in Patients with Cystic Fibrosis", *Chest*, vol. 104, No. 4, Oct. 1993, pp. 1187–1190.

D.M. Hueber, S. Fantini, A.E. Cerussi, B. Barbieri, "New Optical Probe Designs for Absolute (Self–Calibrating) NIR Tissue Hemoglobin Measurements", *Proc. Soc. Photo–Opt. Instrum. Eng.*, 3597, 1999, pp. 618–631.

S. Fantini, M.A. Franceschini, E. Gratton, "Semi–Infinite–Geometry Boundary Problem for Light Migration in Highly Scattering Media: A Frequency–Domain Study in the Diffusion Approximation", *J. Opt. Soc. Am. B.*, vol. 11, Oct. 1994, pp. 2128–2138.

D.T. Delpy, M. Cope, P. van der Zee, S. Arridge, S. Wray, J. Wyatt, Estimation of Optical Pathlength Through Tissue from Direct Time of Flight Measurement, *Phys. Med. Biol.*, vol. 33, No. 12, 1988, pp. 1433–1442.

E.M. Sevick, B. Chance, J. Leigh, S. Nioka, M. Maris, "Quantitation of Time– and Frequency–Resolved Optical Spectra for the Determination of Tissue Oxygenation", *Analytical Biochemistry*, vol. 195, 1991, pp. 330–351.

M. Miwa, Y. Ueka, B. Chance, "Development of Time Resolved Spectroscopy System for Quantitative Non–Invasive Tissue Measurement", *SPIE*, vol. 2389, 1995, pp. 142–149.

S. Fantini, M.A. Franceschini–Fantini, J.S. Maier, S.A. Walker, "Frequency–Domain Multichannel Optical Detector for Noninvasive Tissue Spectroscopy and Oximetry", *Optical Engineering*, vol. 34, Jan. 1995, pp. 32–42.

W.N.J. Colier, J. de Vries, H. van der Zee, M. van der Sluijs, R.J.F. Houston, B. Oeseburg, "Simultaneous, Direct, and Continuous Measurement of Cerebral Hemodynamics and Cerebral Arterial Saturation Using Near Infrared Spectroscopy", Oral Presentation at the BiOS '99 Biomedical Optics Symposium, San Jose, CA, Jan. 23–29, 1999.

* cited by examiner

METHOD FOR MEASURING ABSOLUTE SATURATION OF TIME-VARYING AND OTHER HEMOGLOBIN COMPARTMENTS

This invention was made with Government support under Contract No. PHS5P4103155RR10966, CA57032 awarded by NIH. The Government has certain rights in the invention.

FIELD OF THE INVENTION

The present invention generally concerns a method for optically measuring absolute values of hemoglobin saturation in tissues. More specifically, the present invention concerns non-invasive, real time measures of time-varying hemoglobin compartment saturation.

BACKGROUND OF THE INVENTION

Accurate assessment of oxygen saturation of time varying hemoglobin compartments such as arteries is fundamental to the support of critical-care medicine. Tissue saturation information is also important. Lack of immediate and/or continuous information can lead to potential diagnostic errors, particularly in critically ill patients in whom life-threatening changes can occur rapidly. Arterial compartment saturation measurements are important indicators of vascular oxygen supply. In addition, tissue saturation measurements are important indicators especially during periods of low blood pressure or no pulse.

Various diagnostic measurements are available to assist doctors in determining a patient's oxygenation status, and to protect the patient against dangerous low blood oxygen conditions. Traditionally, blood gases are measured by invasive sampling, either through an indwelling arterial catheter or by arterial puncture. Such sampling, however, can cause significant blood loss, especially for infants. Moreover, since sampled blood is later analyzed in a laboratory, blood gas values are only available after considerable delay.

Beginning in the early 1930's, considerable efforts were made to develop non-invasive optical techniques for accurate measurements of oxygen in the blood. Due to these efforts, the first non-invasive oximeter was developed. Thereafter, known pulse oximetry was introduced in about 1974 and entered clinical practice in the 1980's. It continues to develop, and today pulse oximetry is widely acknowledged as one of the most important technological advances in patient monitoring. An important advantage of pulse oximeters is the capability to provide continuous, safe, and effective monitoring of arterial blood oxygenation non-invasively at a patient's bedside.

Pulse oximetry is based on the physical principle that oxygenated and deoxygenated hemoglobin show different absorption spectra. Deoxygenated hemoglobin absorbs more light in the red band (typically 600 to 750 nm), i.e., it looks less red, and oxygenated hemoglobin absorbs more light in the infrared band (typically 850 to 1000 nm). Thus, known pulse oximeters use one wavelength in the red (typically 660 nm), and one wavelength in the near-infrared (typically 940 nm) spectral range to measure the oxygen saturation of arterial blood. The ratio of light absorbencies at the two wavelengths correlates with a proportion of oxygenated to deoxygenated hemoglobin in tissue, for example, the brain, capillaries, veins, and skeletal muscle. Of all the light absorbed, however, only that absorbed by the pulsating parts of tissue correlates to arterial $O_2$ saturation.

A problem exists with known pulse oximetry since an arterial saturation reading is given on the basis of an empirical scaling. The empirical scaling is based on a preliminary calibration using a population of reference subjects. Due to a lack of physical models, the empirical relationship between a ratio of the pulsatile absorbencies and the arterial saturation is obtained from a large group of healthy volunteers. This empirical scaling relates detected signals to the optical absorption of hemoglobin. Additionally, empirical scaling is accomplished by the use of a continuous wave light which does not afford discrimination of the absorption and the scattering contributions due to light attenuation caused by surrounding tissue. Such empirical scaling has a high potential for error at low saturation (<80%) since manufacturers cannot induce severe hypoxia in volunteers for calibration purposes, and at high saturation (>97%) limits.

Another drawback of conventional pulse oximeters is the requirement to have sensors on either side of an intervening body part to take a reading. Arterial saturation measured in a finger or a toe may not be representative of the systemic arterial saturation ($SaO_2$). Known pulse oximeters work in transmission geometry so that light is transmitted through tissue from one side of a body part, such as a finger, and measured by a photodetector at the other side of the body part. Obviously, such pulse oximeters can only be applied to relatively small body parts such as a finger, toe, earlobe, or nose, but saturation measurements at the brain, for example, are highly desirable.

Additionally, such small body parts only contain peripheral circulation, and local saturation measurements at the periphery may not be indicative of systemic saturation. In infants, for example, the presence of pulmonary hypertension and shunting through a patent ductus arteriosus can make a saturation amount in the foot significantly different from a saturation amount in the head. Furthermore, while changes in pulmonary function can be detected in the ear in a few seconds, it takes as long as 30 seconds to detect in the finger or foot. For these reasons, it is desirable to obtain real time measurements and to measure the local arterial saturation at tissue of interest, typically the brain.

Recently, the introduction of time-resolved optical spectroscopy in conjunction with diffusion theory has lead to quantitative tissue spectroscopy, as described in commonly owned U.S. Pat. No. 5,497,769 to Gratton et al., which is incorporated by reference herein. Known optical tissue oximetry measures the hemoglobin saturation in tissue (y) and is most sensitive to the blood in the capillaries where the oxygen exchange with tissue occurs.

However, known frequency-domain tissue spectroscopy only measures tissue saturation to give indications of tissue oxygen consumption, and do not measure time-varying hemoglobin compartment saturation. Measuring time-varying hemoglobin compartment saturation, such as arterial saturation, is important since such hemoglobin compartment saturation gives indications of vascular oxygen supply, as discussed above. There is a need for time-resolved measurements to provide readings for time-varying hemoglobin compartment saturation, as well as tissue saturation, to yield a balance between a local oxygen supply and oxygen consumption.

Thus, there is a need for an improved method which addresses some or all of the aforementioned drawbacks. A new method should overcome the limitations of known pulse oximetry such as its dependence on an empirical table. Moreover, an improved method should work with arbitrary and desirable tissue locations.

SUMMARY OF THE INVENTION

Such needs are met or exceeded by the present method for measuring absolute saturation of time-varying hemoglobin compartments. A method of the present invention measures time-varying hemoglobin compartment saturation, and preferably also measures tissue saturation simultaneously. The present invention implements time-resolved measurements, using a particular process of data analysis, to achieve absolute pulse oximetry.

The method of the invention is based on the quantitative measurement of tissue absorption spectrum for tissue saturation, and on an intensity of pulsation-induced absorption oscillations for the time-varying hemoglobin compartment saturation, at various wavelengths. The method illuminates at least two tissue locations and detects light at at least two predetermined distances apart. Illumination and detection may be accomplished with a source-detector pair positioned on the common side of a tissue to be measured. Time-resolved measurements of amplitude and phase data are acquired from each source-detector pair. The method then calculates tissue optical properties from the time-resolved measurement data, namely, a reduced scattering coefficient and an absorption coefficient. To determine time-varying hemoglobin compartment saturation, an amplitude of absorption oscillations is quantitatively calculated and correlated to variations of an average amplitude of the source and detector pair by using the time-resolved measurement data. An absolute absorption spectrum of tissue is calculated utilizing the time-resolved measurement data obtained from the source-detector pair.

The invention is applicable to the full range of time-varying hemoglobin compartment saturation values (0–100%). In the particular case of arterial-pulsation-induced absorption oscillations, the method of this invention can measure arterial saturation in the full range 0–100%, rather than limited to the range considered in the instrumental pre-calibration of conventional pulse oximeters. The invention does not depend on inter-subject variability, and it is therefore more accurate than the ±5% (95% confidence interval) afforded by known pulse oximetry. Accuracy and speed are also enhanced by the ability of the invention to measure oxygen saturation at arbitrary bodily locations.

BRIEF DESCRIPTION OF THE DRAWINGS

Other features and advantages of the invention will be apparent to those skilled in the art with reference to the detailed description and the drawings, in which.

DETAILED DESCRIPTION OF THE INVENTION

The present invention yields absolute measurements of tissue saturation (Y) and time-varying hemoglobin compartment saturation, non-invasively and in real time. For exemplary purposes, the invention measures arterial saturation ($SaO_2$) simultaneously with tissue saturation, in substantially the same location. This double reading provides a balance between the local oxygen supply and oxygen consumption that has been unavailable in known instruments. The invention is usable at arbitrary bodily locations and with other time-varying hemoglobin compartments.

Figure 1A:
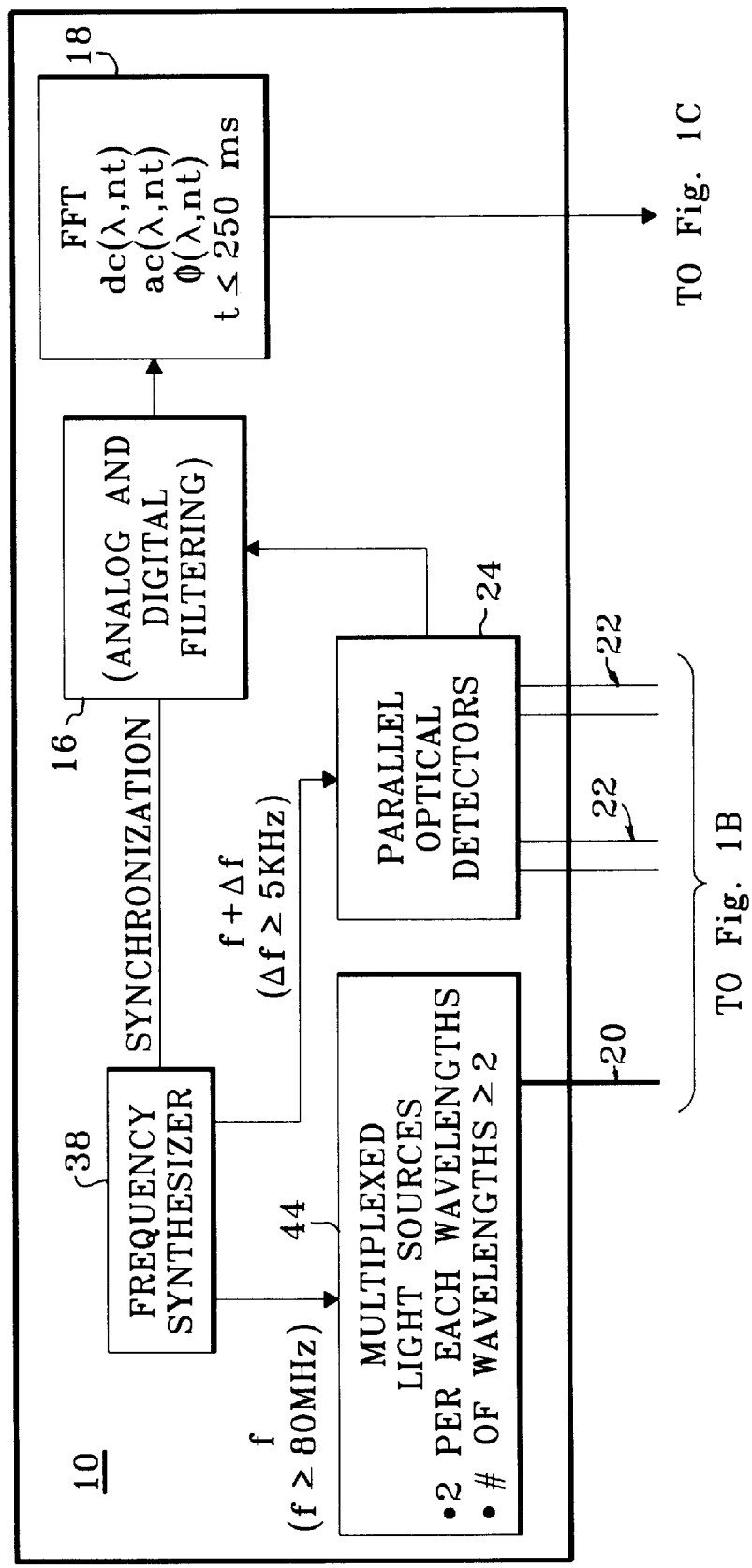
FIGS. 1A–1C are block diagram of a saturation measuring method in accordance with the present invention.
Figure 1B:
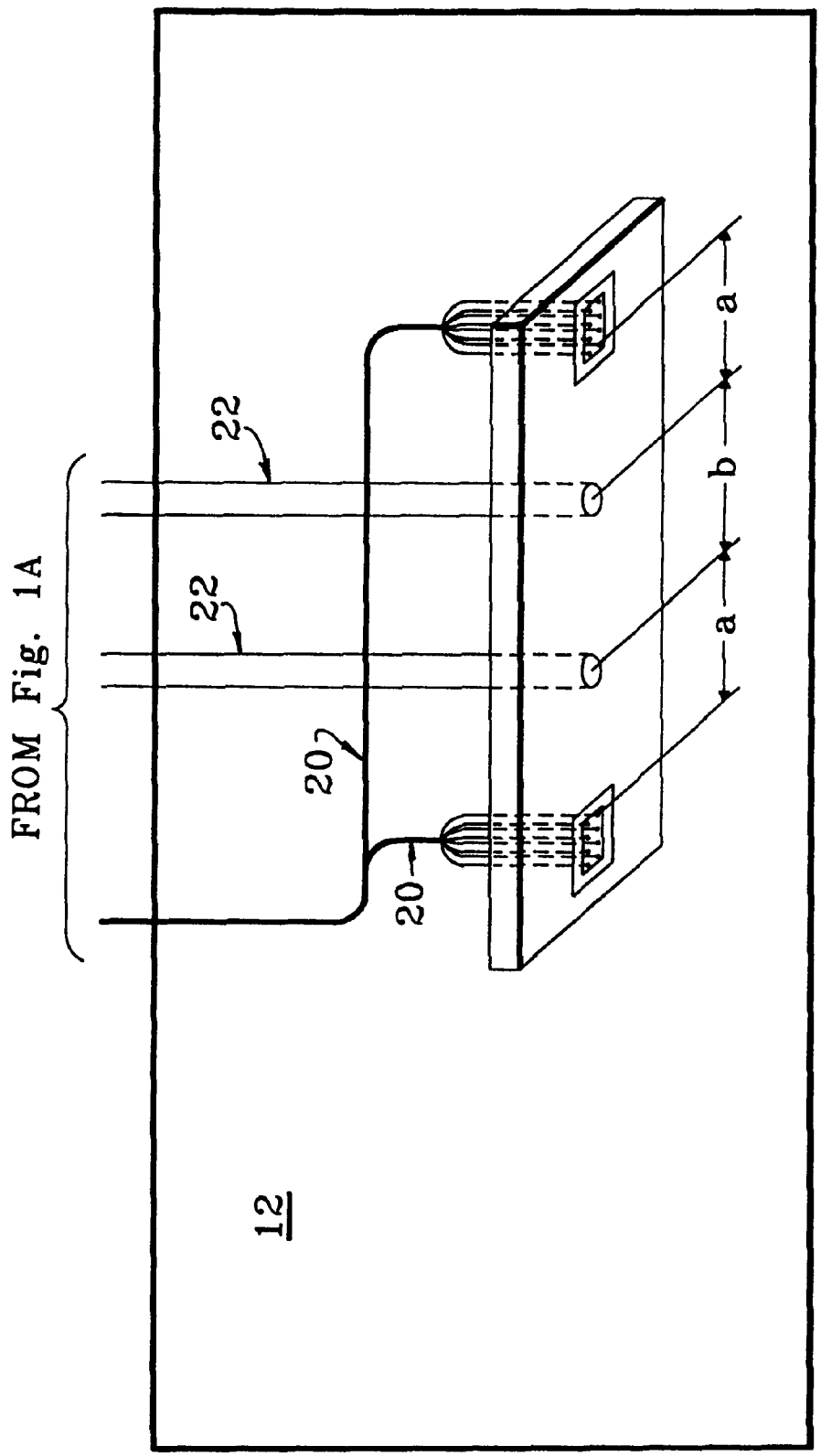
Figure 1C:
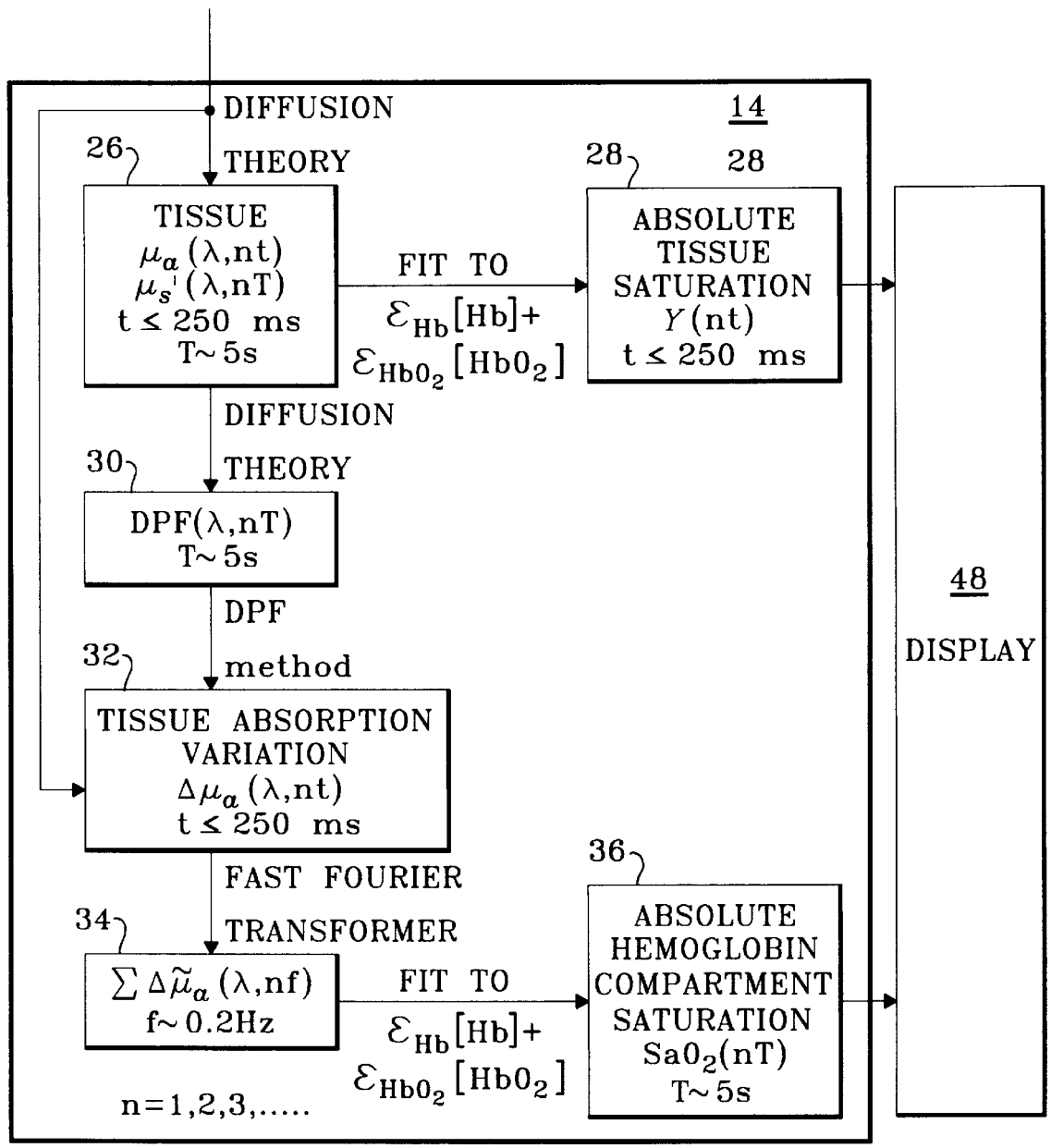

Referring now to the drawings, and particularly FIGS. 1A–1C, the invention as shown includes a frequency-domain spectrometer 10 to obtain time-resolved measurements of phase and amplitude. Artisans will appreciate that optical measurements can be performed with either continuous wave methods, i.e., using constant light intensity, or with time-resolved methods.

Time-resolved methods include the time-domain where light intensity is pulsed with a pulse width in the order of picoseconds or less, and the frequency-domain, where light intensity is sinusoidally modulated at a radio frequency. In the time-domain, one measures the time-of-flight distribution of detected photons, whereas in the frequency-domain an average intensity, the amplitude, and a phase of a detected modulated intensity are measured. The time-domain and the frequency-domain methods are mathematically related by a temporal Fourier transform. Thus, the time-domain method is equivalent to a collection of frequency-domain measurements over a band of modulation frequencies. For exemplary purposes, the present invention is described with the frequency-domain approach to an absolute measurement of hemoglobin saturation. However, the same method described is applicable in the time-domain. One aspect of the invention is the use of a time-resolved optical method, which is performed in either the frequency-domain or the time-domain. Importantly, time-resolved methods allow the separation of reduced scattering and absorption coefficients of tissues. The separation of reduced scattering and absorption coefficients of tissues allows for absolute absorption measurements and, therefore, absolute concentration measurements.

Artisans will appreciate that in frequency-domain spectroscopy the intensity of the light source is modulated at a radio frequency f, preferably 110 MHz, and the detector sensitivity is modulated at a frequency f+Δf, where the offset frequency Δf is lower than f, preferably in the kHz range. It is noted, however, that radio frequencies other than 110 MHz are viable, being limited only by the fact that too low a radio frequency results in inadequate phase shift and too high a radio frequency will be outside a range of known detectors' capabilities.

The frequency-domain spectrometer 10 connects to an optical probe 12 and a processor 14 for analyzing data from the frequency-domain spectrometer 10 and optical probe 12. Detector output is passed through a low-pass filter 16 and is processed in a fast Fourier transformer (FFT) 18 to provide an average intensity (dc), an amplitude (ac), and a phase (Φ), i.e., time-resolved measurement data, of the detected signal at frequency f.

Optical probe 12 preferably contains optical source fibers 20 that guide light to tissue to be examined, and detector fibers 22 that guide the collected light from tissue to an optical detector 24, such as a photomultiplier tube or photo sensor. The probe 12 should preferably be light weight and partially flexible to adapt to the surface of the examined tissue, but its shape should remain substantially unaltered in order to maintain a well defined and fixed geometrical relationship between the source fibers 20 and detector fibers 22. The optical probe 12 is designed to afford quantitative tissue spectroscopy without requiring any sort of instrumental calibration.

To position both the source fibers 20 and detector fibers 22 of the optical probe 12 on the common side of the tissue sample, the present method uses diffused reflection geometry. This feature allows the optical probe 12 to be applied to any tissue of interest.

Referring now to the process of data analysis, the processor 14 operates so that a pulsatile component of tissue absorption can be quantified to produce absolute values of time-varying hemoglobin compartment and/or tissue saturation. A first step of the analysis consists of a quantitative determination of a tissue reduced scattering coefficient ($\mu_s'$) and an absorption coefficient ($\mu_a$) (block 26 in FIG. 1). To this aim, a multi-distance method is applied using two or more source-detector separation distances (a and a+b). This is achieved by using multiple sources either multiplexed or modulated at different frequencies to electronically distinguish the corresponding signals and/or multiple detectors which can acquire data in parallel, or sequentially. Additionally, this can be achieved by moving a source with respect to a detector over the desired range of source-detector separation.

The multi-distance time-resolved measurement method assumes a homogeneous and semi-infinite geometry. The absolute values of the absorption ($\mu_a$) and reduced scattering ($\mu_s'$) coefficients of tissue are given in terms of the dc, ac, and phase slopes versus source-detector separation ($S_{dc}$, $S_{ac}$, and $S_\Phi$, respectively). In particular, either the $S_{dc}$ and $S_\Phi$ pair, or the $S_{ac}$ and $S_\Phi$ pair can be used to measure $\mu_a$ and $\mu_s'$. US Using dc and phase:

$$\mu_s' = \frac{2\upsilon}{3\omega} S_\Phi (S_\Phi^2 + S_{dc}^2)^{1/2}, \quad (1)$$

$$\mu_a = \frac{S_{dc}^2}{3\mu_s'}, \quad (2)$$

using ac and phase:

$$\mu_s' = -\frac{2\nu}{3\omega} S_\Phi S_{ac}, \quad (3)$$

$$\mu_a = \frac{S_{ac}^2}{3\mu_s'}\left[1 - \left(\frac{3\omega \mu_s'}{2\nu S_{ac}^2}\right)^2\right] \quad (4)$$

where ω is the angular modulation frequency of the source intensity, and υ is the speed of light in tissue.

Importantly, the present method averages the $\mu_s'$ measurement on a time scale T, which is longer than a data acquisition time t, where the data acquisition time t is equal to or less than about one-half a period of oscillation. For example, for a data acquisition time of t≦250 ms, a$\mu_s'$ measurement time T is approximately 5 seconds. The longer time scale allows the present invention to maintain a high temporal resolution in the absorption measurement, while drastically reducing the contribution of the phase noise because the phase data only appears in the expression for $\mu_s'$ which is averaged over time T. The only assumption of this method is that the reduced scattering coefficient $\mu_s'$ does not vary on a time scale faster than T, which is generally true for T in the order of a few seconds.

To measure tissue saturation Y, the spectrum of the tissue absorption is fit with a linear combination of the extinction spectra of oxy-hemoglobin and deoxy-hemoglobin. The fitted parameters are the concentrations of oxy-hemoglobin ([HbO$_2$]) and deoxy-hemoglobin ([Hb]). Tissue saturation Y is then given by the expression [HbO$_2$]$_t$/([HbO$_2$]$_t$+[Hb]$_t$), where the subscript "t" indicates that the involved concentrations refer to tissue (block 28). Since tissue saturation Y is determined by absorption $\mu_a$ and not by scattering $\mu_s'$, the present invention achieves an absolute measurement of tissue saturation Y with a fast temporal resolution and having excellent signal-to-noise ratio characteristics.

In addition to the above measured tissue saturation Y, the time-resolved measurements of the present invention are used to simultaneously measure the saturation of time-varying hemoglobin compartments. For exemplary purposes, we describe the absolute measurement of arterial saturation (SaO$_2$). The arterial hemoglobin concentration in tissue oscillates with time as a result of the arterial pulsation associated with the systolic/diastolic pressure variation. Consequently, the detected oscillations in the optical signal at the frequency of the heart rate can be assigned to the arterial hemoglobin compartment, whose saturation is then related to the oscillatory components of the absorption coefficients at two or more wavelengths.

To perform absolute pulse oximetry using the time-resolved measurements of the present invention, an amplitude of the pulsation-induced absorption oscillations is quantitatively measured. The absorption oscillations ($\Delta\mu_a$) are effectively measured by the variations in the average intensity at each source-detector pair using a known differential path length factor (DPF) method (see Delpy et al., Phys. Med. Biol. 33, 1433 (1988), incorporated by reference herein) (block 30 in FIG. 1):

$$\Delta\mu_a(t) = \frac{1}{rDPF} \ln\left[\frac{dc(0)}{dc(t)}\right], \quad (5)$$

where r is the source-detector distance, and dc(O) and dc(t) are the average intensities measured at time zero and time t, respectively.

The DPF method requires the knowledge of the average photon path-length in tissue, which varies for different individuals, different tissues, and different locations within a tissue, and of its wavelength dependence. Since assuming a wrong wavelength dependence of the DPF can lead to significant errors in the measured time-varying hemoglobin compartment saturation, the present invention takes advantage of the time-resolved measurement data, gathered earlier, to measure the DPF spectrum, rather than relying on empirical DPF spectra:

$$DPF = \frac{\sqrt{3\mu_s'}}{\sqrt{\mu_{a0}^2}}\left(\frac{\sqrt[r]{3\mu_{a0}\mu_s'}}{\sqrt[r]{3\mu_{a0}\mu_s'} + 1}\right) \quad (6)$$

where $\mu_{a0}$ is an average (non pulsatile) absorption coefficient.

The present invention evaluates the amplitude of the pulsation-induced absorption variations by taking the sum of the amplitudes of the fast Fourier transform (FFT) of $\Delta\mu_a$ over the heartbeat band (blocks 32 and 34 in FIGS. 1A–1C). The FFT of $\Delta\mu_a$ is evaluated over sixteen, thirty-two, or sixty-four points, for example, corresponding to time traces approximately 4, 8, or 16 seconds long (block 32). To achieve reliable and reproducible spectra from a number of heartbeat periods, a time period considered should generally be in the order of several periods of oscillation. Thus, where an artery oscillates about once a second, the time trace to be fast Fourier transformed should be at least several seconds long.

Gathered time-resolved measurement data is important in this invention to achieve absolute pulse oximetry. Indeed, both amplitude and phase data are used to measure the reduced scattering coefficient of tissue (in determination of Y) and the spectrum of the DPF (in determination of $SaO_2$). To measure the time-varying hemoglobin compartment saturation, the present invention fits the spectrum of the pulsatile amplitude of the absorption oscillations with a linear combination of the extinction spectra of oxy-hemoglobin and deoxy-hemoglobin. The fitted parameters are the concentrations of oxy-hemoglobin ($[HbO_2]$) and deoxy-hemoglobin ($[Hb]$). The arterial hemoglobin saturation is then given by the expression $[HbO_2]_p/[HbO_2]_p + [Hb]_p$), where the subscript "p" indicates the pulsatile origin (block 36).

Artisans will appreciate that this approach to absolute pulse oximetry lends itself to the saturation measurement of other hemoglobin oscillations observed in tissues. For instance, vasoconstriction activity gives rise to hemoglobin concentration waves with a period in the order of 10 to 15 seconds, while waves at the respiratory period (~3–8 seconds) are observed as well. Thus, it is appreciated that this invention is not limited to absolute pulse oximetry, but its basic approach can be generally applied to absolute saturation measurements of time-varying hemoglobin compartments.

Figure 2:
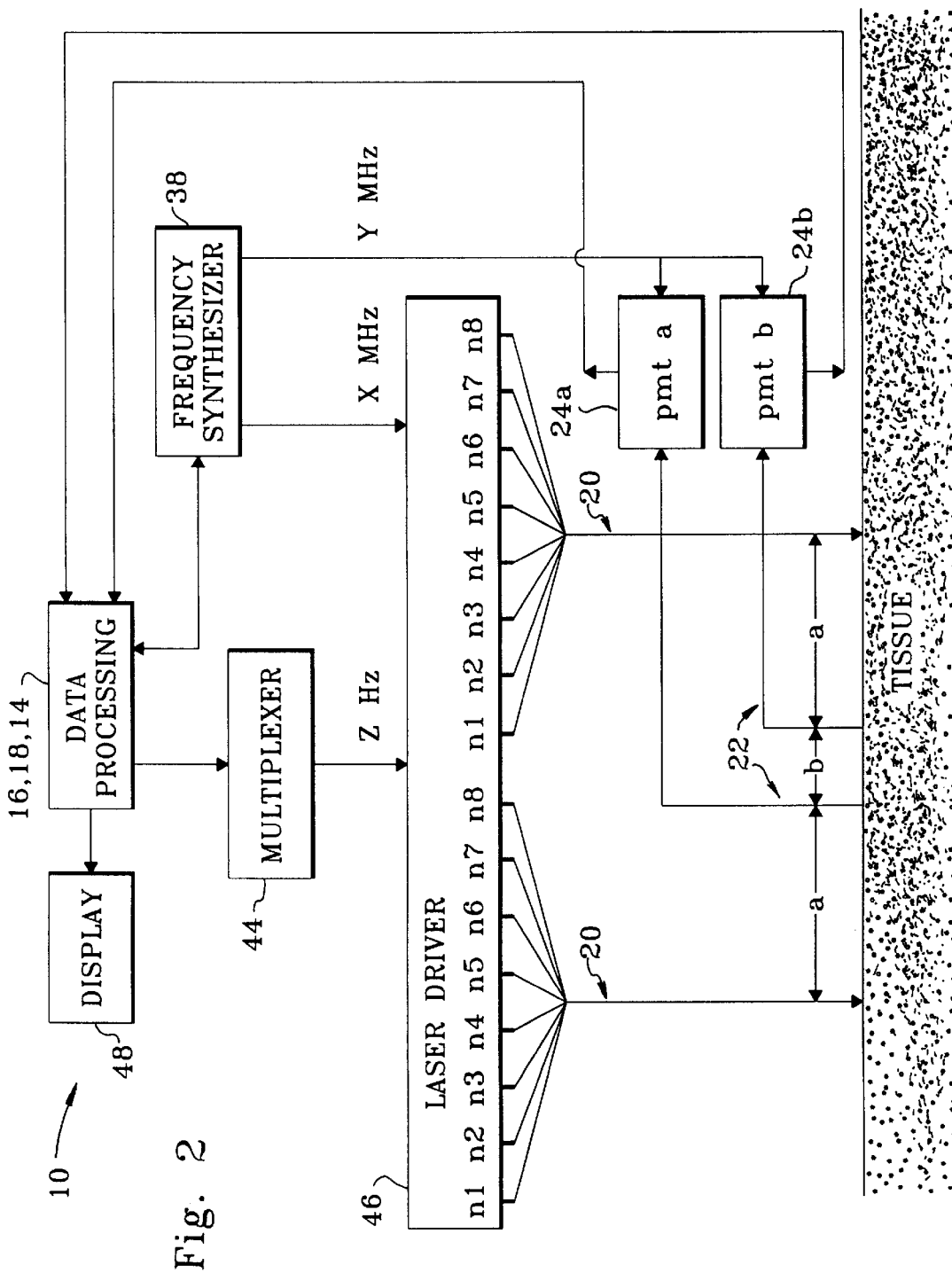
FIG. 2 is a block diagram of a frequency-domain tissue spectrometer and optical probe used in the saturation measuring method shown in FIGS. 1A–1C.

Referring now to FIG. 2, the preferred embodiment of the invention uses a frequency-domain tissue spectrometer 10 (see also FIG. 1A) including a frequency-synthesizer 38 to modulate the intensity of laser diodes at a frequency of x MHz, e.g, 110 MHz. The frequency-synthesizer 38 also modulates a second dynode of two photo multiplier tubes (pmt), pmt a 24a and pmt b 24b, of the optical detector 24 (FIG. 1A), at a frequency of y MHz, e.g., 110.005 MHz. Artisans will appreciate that other optical detectors can be used, but photo multiplier tubes are preferred for their sensitivity.

The frequency-domain spectrometer operates at at least two wavelengths in a range from about 600 to 1000 nm. For exemplary purposes, eight discrete wavelengths n1–n8 (for example 633, 670, 751, 776, 786, 813, 830, 841 nm) were used in the red and near-infrared spectral region. Artisans will appreciate that other similar wavelengths may be used. It is noted that optical spectroscopy in the wavelength range from 600 to 1000 nm achieves a sufficient photon penetration depth to non-invasively probe macroscopic tissue volumes and remains sensitive to oxygen saturation of hemoglobin.

A multiplexer 442 multiplexes the light sources, two laser diodes contained in a laser driver 46 per each wavelength, at a rate of z Hz, e.g., 71.4 Hz, to time-share the two parallel detectors 22 so that each light source is on for approximately 14 ms. Therefore, the total acquisition time for a full cycle over the light sources is 224 ms. The multiplexer 442 electronically multiplexes the light sources at a rate z such that $N/z \leq P/2$, with N total number of light sources, and P period of oscillation of the time-varying hemoglobin compartment to be measured. A time resolution of 224 ms is sufficient to monitor the dynamics of the arterial pulsation, which occurs on a time scale of about 1 second. In this example, two parallel detectors 24 collect data at two tissue locations, simultaneously.

Each one of sixteen laser diodes is coupled to an optical fiber approximately 400 µm in core diameter. The preferred embodiment groups the two sets of eight fibers guiding light at the eight wavelengths into two source fiber bundles 20 having a rectangular section of internal size, for example, 2.4×1.2 mm². The optical signal detected on tissue is guided to two parallel detector channels of the spectrometer by two optical detector fiber bundles 22, for example, 3 mm in internal diameter. The source fibers 20 and the detector fibers 22 are placed on the common side of the examined tissue, for example a forehead, in the symmetrical configuration shown in FIG. 2.

This geometrical arrangement of the source fiber 20 and the detector fibers 22 features four distinct source-detector pairs, and two distinct source-detector separations (a and a+b), for example 3.0 cm and 3.6 cm where a is 3 cm and b is 0.6 cm. Artisans will appreciate that other distances between the source and detector fibers are contemplated. To determine a geometrical arrangement of the source fibers 20 and the detector fibers 22, the distance a should be greater than, or in the order of, 1.5 cm to achieve a sufficient optical penetration depth into the tissue. In addition, a+b should be less than, or in the order of, 4 cm to collect data with a high signal-to-noise ratio. Moreover, b should assume values between about 0.5 cm and about 2 cm to be large enough to distinguish different signals at separations a and a+b, and small enough to ensure that the signals at separations a and a+b probe essentially the same tissue volume.

The outputs of pmta 24a and pmtb 24b are processed in the data processing apparatus 16, 18, 14, as seen in FIG. 2, and the results are provided in a display 48.

This source-detector configuration affords quantitative spectroscopy independent of source, detector, and optical-coupling terms, i.e., without requiring instrumental calibration. To avoid pre-calibration, the present invention relies on a physical model to quantitatively describe the relationship between the collected optical signal and tissue optical properties. This model, which assumes a macroscopically uniform distribution of the time-varying hemoglobin compartment pulsation in tissue, is well justified in most cases, but there may be cases where its assumptions are not fulfilled. A way to overcome this is to include a self-check feature in an instrument that verifies whether the data is consistent with the model. If the data is not consistent, the probe is re-positioned to a nearby location.

The present invention was tested using a measurement protocol that involves a change in the oxygen concentration inspired by the subject. For example, a healthy volunteer breathed a 21% oxygen concentration by volume of room air for one minute. Thereafter, the inspired oxygen concentration was lowered to 10% by volume for one minute, and finally brought back to 21%. Absolute tissue spectroscopy was performed using the multi-distance time-resolved measurement method of the present invention described above, assuming a homogeneous and semi-infinite geometry.

To maximize the signal-to-noise ratio, the calculation of $\mu_s'$ was updated every 10 seconds. In this way, the contribution of the phase noise to the measurement of $\mu_a$ is strongly reduced, whereas the 224 ms acquisition time for the absorption spectrum was maintained. The amplitude of the pulsation-induced absorption variations were evaluated by taking the sum of the amplitudes of the fast Fourier transform (FFT) of $\Delta\mu_a$ over the heartbeat band. For example, the FFT of $\Delta\mu_a$ were evaluated over sixty-four points, corresponding to a time trace 14.3 seconds long, to achieve reliable and reproducible spectra from a number of heartbeat periods. The absorption oscillations at the eight wavelengths were verified as being in phase by measuring the relative phase of FFT of the absorption traces at the heartbeat frequency.

Figure 3:
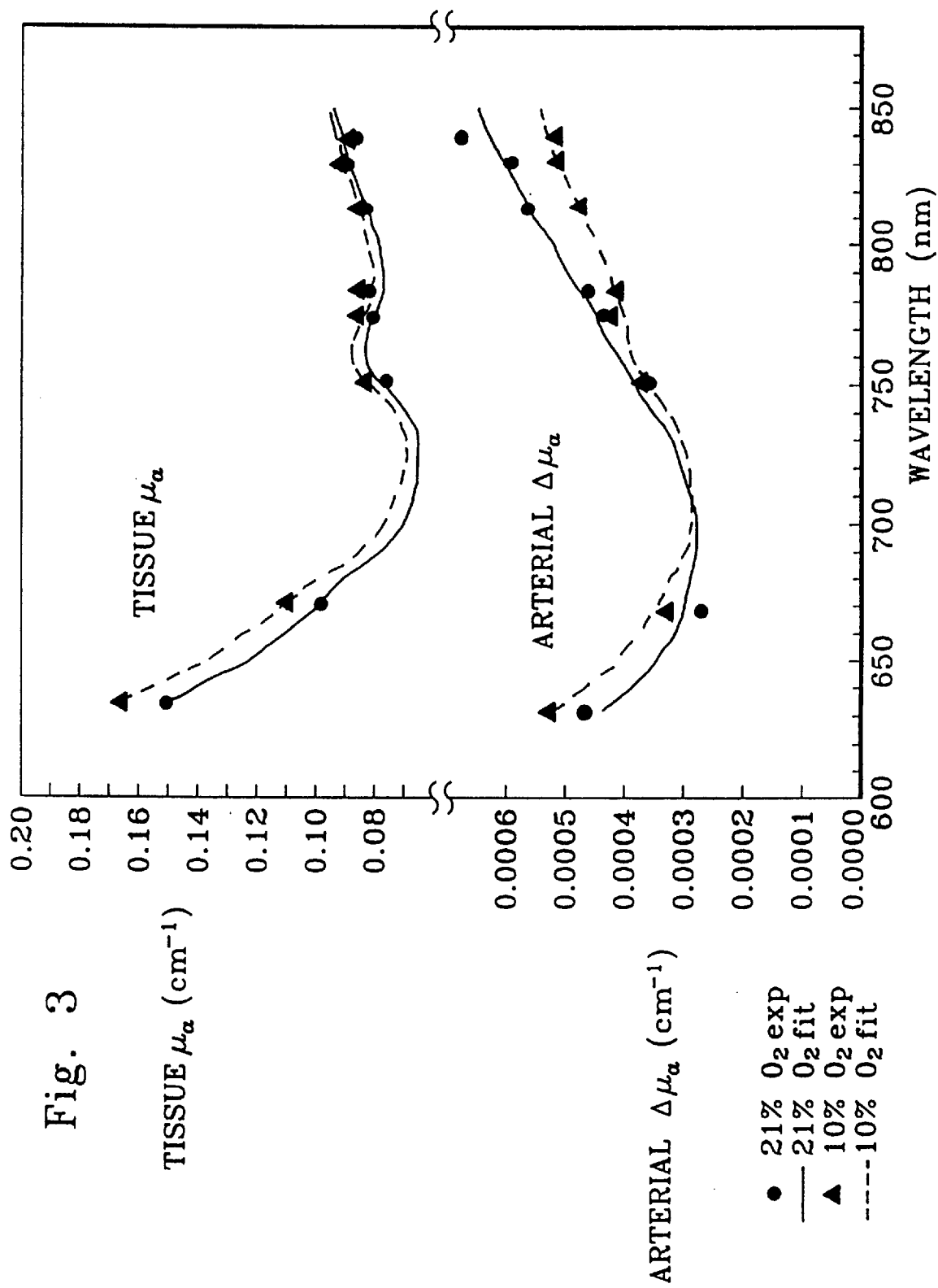
FIG. 3 is a graph produced with data acquired using the present saturation measuring method to measure the effect of a reduced inspired oxygen concentration on a tissue absorption spectrum and time-varying hemoglobin compartment absorption.

Referring now to FIG. 3, to measure the hemoglobin saturation, an absolute absorption spectrum for tissue saturation and the spectrum of the pulsatile amplitude of the absorption oscillations for the time-varying hemoglobin compartment saturation, are fitted with a linear combination of the extinction spectra of oxy-hemoglobin and deoxy-hemoglobin, as described above. For exemplary purposes, the spectra of the amplitude of the absorption oscillations at the heartbeat frequency are shown under baseline conditions of 21% inspired oxygen, and at maximal desaturation induced by 1 minute of 10% inspired oxygen concentration. The symbols are the experimental data measured on the forehead to measure local absorption and saturation in the brain. Artisans will appreciate, however, that the invention can be arbitrarily applied to other tissues as well because its sensors are generally disposed in parallel on the common side of a tissue sample.

The lines are the best fits of the data with a linear combination of the extinction spectra of oxy-hemoglobin and deoxy-hemoglobin. The saturation values corresponding to the four fitted spectra are reported below in the Table. The Table shows tissue saturation (Y) and arterial saturation ($SaO_2$) in the forehead measured by the present invention, and arterial saturation measured on the index finger by a known commercial pulse oximeter (Pulse Ox.). The known commercial pulse oximeter data is used to show that the present invention successfully achieves accurate time-varying hemoglobin compartment (in this case, arterial) saturation readings and simultaneously achieves tissue saturation readings not available with conventional devices. The first row refers to a baseline condition of 21% by volume inspired oxygen concentration, and the second row refers to maximal desaturation conditions after the inspired oxygen concentration was decreased to 10% for 1 minute.

| Condition | Y (%) Invention | $SaO_2$ (%) Invention | $SaO_2$ (%) Pulse Oximeter |
|---|---|---|---|
| Baseline | 74.7 ± 0.2 | 96.9 ± 0.5 | 97 |
| Maximal Desaturation | 71.6 ± 0.2 | 90.0 ± 0.5 | 91 |

Figure 4:
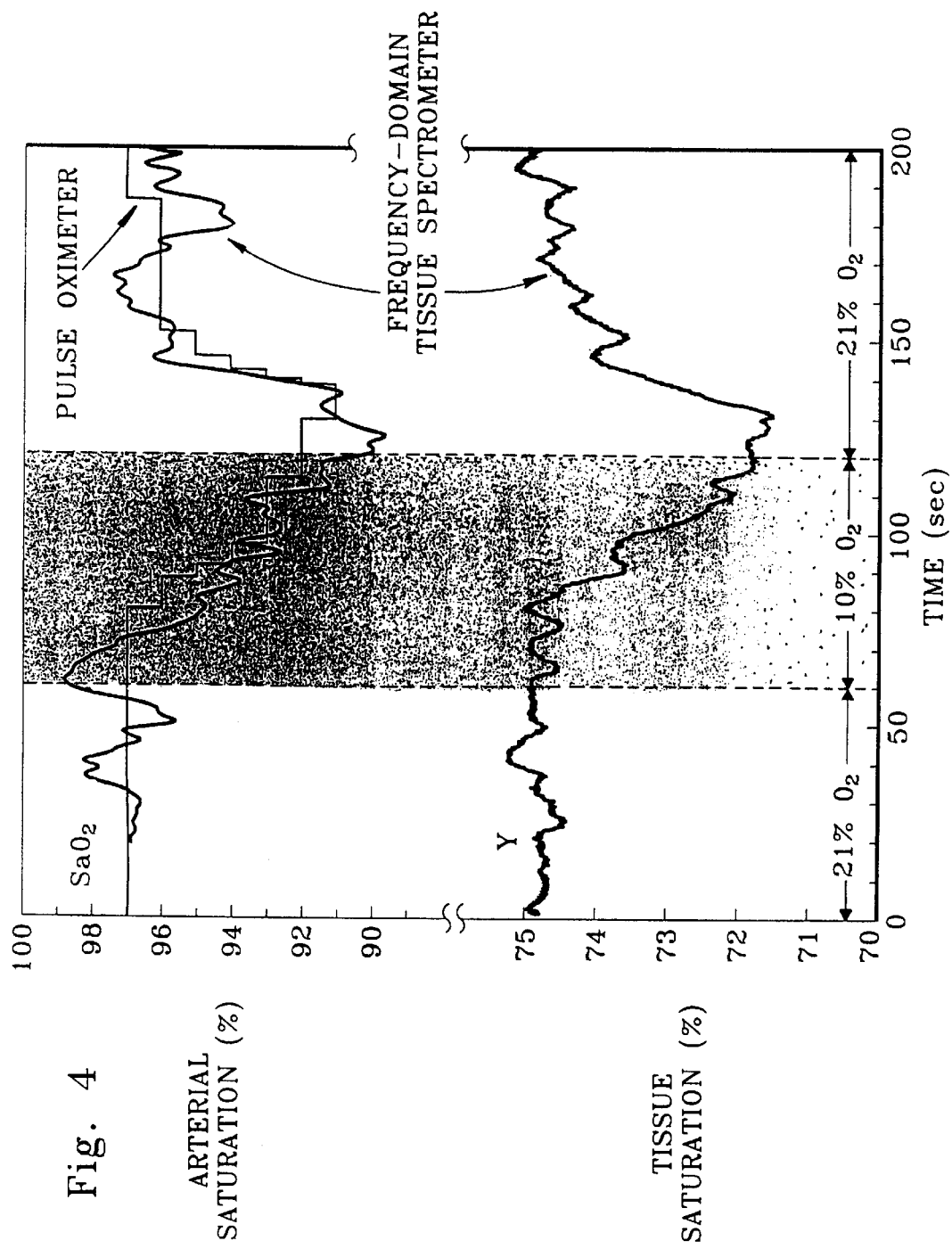
FIG. 4 is a graph of time traces of tissue saturation Y and arterial saturation $SaO_2$ measured with the method of the present invention, and arterial saturation measured with a known commercial pulse oximeter.

Referring now to FIG. 4, shown are the exemplary time traces of $SaO_2$ recorded in real time. The area within dotted vertical lines indicates the period of reduced inspired oxygen concentration, i.e., 10% by volume, from a baseline value of 21%. Software, for example, can implement the process discussed above for data analysis to give direct readings on-line. As shown, the values of time-varying hemoglobin compartment, in this case arterial, saturation measured with the present absolute spectroscopic method and with the commercial pulse oximeter are in excellent agreement throughout the experiment.

From the foregoing description, it should be understood that an improved method has been shown and described which has many desirable attributes and advantages. A time-resolved measurement approach is presented to non-invasively measure the absolute value of time-varying hemoglobin compartment saturation in real time. In addition, an absolute value of tissue saturation can be simultaneously measured. Good fits obtained using at least two wavelengths confirm that oxy-hemoglobin and deoxy-hemoglobin are major species contributing to the absorption spectra. The present approach provides more complete information than known oximetry about tissue oxygenation level, provides local time-varying hemoglobin compartment saturation of the brain, and can be applied over the full range of time-varying hemoglobin compartment saturation values. Absolute saturation is measured without calibration based on a population of healthy subjects. In addition, the invention is applicable to arbitrary bodily locations.

Other alterations and modifications will be apparent to those skilled in the art. Accordingly, the scope of the invention is not limited to the specific embodiments used to illustrate the principles of the invention. Instead, the scope of the invention is properly determined by reference to the appended claims and any legal equivalents thereof.

What is claimed is:

1. A method of measuring absolute saturation of hemoglobin compartments, the method comprising the steps of:
    illuminating an area of tissue with intensity-modulated light at at least two wavelengths;
    sensing diffusely reflected light caused by said illumination to acquire time-resolved measurement data; and
    processing said time-resolved measurement data to determine the absolute saturation of a hemoglobin compartment, without calibration on a population of healthy subjects;
    wherein the absolute saturation of hemoglobin determined by said processing step includes absolute arterial saturation; and
    wherein an amplitude of pulsation-induced absorption oscillations are quantitatively determined in said processing step to perform absolute pulse oximetry.

2. The method according to claim 1, wherein said hemoglobin compartments include a time-varying hemoglobin compartment, and said time-resolved measurement data includes at least two readings per period of oscillation of the time-varying hemoglobin compartment.

3. The method according to claim 1, wherein said intensity-modulated light is modulated with components in a radio frequency range.

4. The method according to claim 1, wherein said wavelengths are in the visible and near-infrared spectral range.

5. The method according to claim 1, wherein said processing step includes a step of determining a reduced scattering coefficient to determine an oscillation of the absorption coefficient of tissue using said time-resolved measurement data, said oscillation absorption coefficient being used to determine the absolute saturation of the hemoglobin compartment.

6. The method according to claim 5, where said reduced scattering coefficient is averaged over multiple readings to increase a signal-to-noise ratio in the measurement of the absorption coefficient.

7. The method according to claim 5, wherein said processing step further includes a step of periodically updating said reduced scattering coefficient.

8. The method according to claim 1, wherein said hemoglobin compartments include time-varying hemoglobin compartments and tissue hemoglobin compartments, and said absolute saturation of said hemoglobin compartment and said tissue saturation are determined simultaneously.

9. The method according to claim 1, wherein said steps of illuminating and sensing are conducted on a common side of said area of tissue.

10. A method of measuring absolute saturation of hemoglobin compartments, the method comprising the steps of:
    illuminating an area of tissue with intensity-modulated light at at least two wavelengths;
    sensing diffusely reflected light caused by said illumination to acquire time-resolved measurement data; and
    processing said time-resolved measurement data to determine the absolute saturation of a hemoglobin compartment, without calibration on a population of healthy subjects;
    wherein said hemoglobin compartments include time-varying hemoglobin compartments, and said processing step includes a step of calculating the sum of amplitudes of a fast Fourier transformed absorption coefficient for a predetermined time period to determine an amplitude of absorption oscillations.

11. The method according to claim 10, wherein said predetermined time period is at least as long as, several periods of oscillation of said time-varying hemoglobin compartments.

12. The method according to claim 11, wherein the time-varying hemoglobin compartment saturation is determined by fitting a spectrum of said amplitude of absorption oscillations with a linear combination of extinction spectra of oxy-hemoglobin and deoxy-hemoglobin.

13. A method of measuring absolute saturation of hemoglobin compartments, the method comprising the steps of:

illuminating at least two areas of tissue with intensity-modulated light at at least two wavelengths;

sensing diffusely reflected light at at least two locations of said illuminated tissue to acquire time-resolved measurement data; and processing said time-resolved measurement data to simultaneously determine the absolute saturation of at least one hemoglobin compartment;

wherein the absolute saturation of hemoglobin determined by said processing step includes absolute arterial saturation;

wherein an amplitude of pulsation-induced absorption oscillations are quantitatively determined in said processing step to perform absolute pulse oximetry.

14. The method according to claim 13, wherein said hemoglobin compartments include a time-varying hemoglobin compartment, and said time-resolved data includes phase and intensity data and said step of processing determines a reduced scattering coefficient of tissue to determine the absolute saturation of the time-varying hemoglobin compartment.

15. The method according to claim 13, wherein said sensing step and said illuminating step are conducted on a common side of said illuminated tissue.

* * * * *

UNITED STATES PATENT AND TRADEMARK OFFICE
CERTIFICATE OF CORRECTION

PATENT NO. : 6,216,021 B1
DATED : April 10, 2001
INVENTOR(S) : Franceschini et al.

It is certified that error appears in the above-identified patent and that said Letters Patent is hereby corrected as shown below:

Column 2,
Line 45, delete "(y)" and insert -- (Y) -- thereto

Column 5,
Line 28, delete "us"

Column 6,
Line 42, delete the current equation and insert $$DPF = \frac{\sqrt{3\mu_s'}}{2\sqrt{\mu_a 0}} \left( \frac{r\sqrt{3\mu_{a0}\mu_s'}}{r\sqrt{3\mu_{a0}\mu_s'}+1} \right)$$

Column 7,
Line 47, delete "442" and insert -- 44a -- thereto
Line 52, delete "442" and insert -- 44a -- thereto Signed and Sealed this Twenty-sixth Day of February, 2002

Attest:

JAMES E. ROGAN
Attesting Officer
Director of the United States Patent and Trademark Office